United States Patent
Jain et al.

(10) Patent No.: US 12,297,478 B2
(45) Date of Patent: May 13, 2025

(54) INDUSTRIALLY USEFUL STRAINS OF YEAST

(71) Applicant: PRAJ INDUSTRIES LIMITED, Pune (IN)

(72) Inventors: Rishi Jain, Hinjewadi (IN); Dheeraj Madhukar Mahajan, Hinjewadi (IN); Sanjay Ratilal Mistry, Hinjewadi (IN); Rutuja Shivaji Jagtap, Hinjewadi (IN); Megha Shaligram Bilaiya, Hinjewadi (IN); Rajesh Kumar Singh, Hinjewadi (IN); Ghansham Baburao Deshpande, Hinjewadi (IN); Pramod Shankar Kumbhar, Hinjewadi (IN)

(73) Assignee: PRAJ INDUSTRIES LIMITED (IN)

( * ) Notice: Subject to any disclaimer, the term of this patent is extended or adjusted under 35 U.S.C. 154(b) by 733 days.

(21) Appl. No.: 16/772,297

(22) PCT Filed: Nov. 28, 2018

(86) PCT No.: PCT/IN2018/050792
§ 371 (c)(1),
(2) Date: Jun. 12, 2020

(87) PCT Pub. No.: WO2019/116382
PCT Pub. Date: Jun. 20, 2019

(65) Prior Publication Data
US 2021/0071206 A1    Mar. 11, 2021

(30) Foreign Application Priority Data
Dec. 12, 2017 (IN) .............................. 201721044702

(51) Int. Cl.
| | |
|---|---|
| *C12N 1/00* | (2006.01) |
| *C12N 15/81* | (2006.01) |
| *C12P 7/16* | (2006.01) |
| *C12N 1/18* | (2006.01) |
| *C12R 1/865* | (2006.01) |

(52) U.S. Cl.
CPC ................ *C12P 7/16* (2013.01); *C12N 15/81* (2013.01); *C12N 1/185* (2021.05); *C12R 2001/865* (2021.05)

(58) Field of Classification Search
CPC ..... Y02E 50/10; C12N 15/11; C12N 15/1079; C12N 1/18; C12N 15/81; C12N 1/185; C12N 15/80; C12P 7/06; C12P 7/16
USPC ......................... 435/161, 157, 254.21, 320.1
See application file for complete search history.

(56) References Cited

FOREIGN PATENT DOCUMENTS

| | | |
|---|---|---|
| CN | 102329743 A | 1/2012 |
| WO | 2014048863 A1 | 4/2014 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
International Search Report & Written Opinion for PCT/IN2018/050792, dated Jun. 20, 2019.
Hubbman, "Application of novel metabolic engineering tools for engineering of the complex trait of glycerol yield in *Saccharomyces cerevisiae*", Thesis—dissertation, KU Leuven, Faculty of Science, Engineering & Technology, 2013, 1-198.
Hubbmann, et al., "Identification of multiple interacting alleles conferring low glycerol and high ethanol yield in *Saccharomyces cerevisiae* ethanolic fermentation", Biotechnology for Biofuels, vol. 6, Issue: 87, 2013, 1-17.

* cited by examiner

*Primary Examiner* — Robert B Mondesi
*Assistant Examiner* — Mohammad Y Meah
(74) *Attorney, Agent, or Firm* — Billion & Armitage

(57) ABSTRACT

The invention relates to a method for the preparation of industrially useful strains of yeast *Saccharomyces cerevisiae* and the strain prepared by the method. In particular the invention relates to the creation of double mutant strains of the yeast that shows high ethanol conversion efficiency and substantially reduced acetic acid and glycerol production during fermentative production of ethanol from a sugar-based feedstock.

12 Claims, 3 Drawing Sheets
Specification includes a Sequence Listing.

SEQUENCE LISTING

<160> NUMBER OF SEQ ID NOS: 2

<210> SEQ ID NO 1
<211> LENGTH: 2229
<212> TYPE: DNA
<213> ORGANISM: Saccharomyces cerevisiae

<400> SEQUENCE: 1

```
ctgctgtaaa tcaaaaacga atcgattttg gggagacaag taaaaatgct caattctgcg      60
ttactgtgga aggtttggct acgaatagac aactccactg atgaagtaaa ccaaccaatt     120
gctgtacagt tcgatgaaat agatactgtt gatgatttga agagcaggtt ttttcagaaa     180
ctgagttcga ctcgatggcg agaaattaac gataatgctt ccattgcaat aggcctctac     240
gcacctaaat ttgacaatca agccgacaat accagtagta acaacactaa cgataatagt     300
tgtcgaagta agagtaacgg tgctggaagt ggcgccaacc tttccgttaa tagcaatacc     360
aagagttcag tgagccccac agcaggatca tttggtcttt caaagacct tgcaaaggac      420 aggaatgttc tccagcatcc taaacctacg cagaaaagag gagcattata cgacgccttt     480
gccgccgcgc cgacagtggc cgcgactacc aatgtggatt ttcctcccaa cgaggcgcca     540
atgctaagcc cgcaaagacc atactctact agtcctaaac agtttccagc aacaactaaa     600
agtccgttac tgcgatttgc ctcagtctca ccctacccta aatttcatcc tgataatcaa     660
attatggcat cagctggtct tacatacgtc tcaccgcata ataaaaataa atacacaagg     720
ccgttgatta gaaaaggttt aaatttcacc acagaatcag ttaatgattg cacttataaa     780
atcatctttg aaccggatga attggctatt aacatatata aggaactgtt cggaaccatg     840
ggttcccaac ctgcatcgca gcctttgctg atattttcga atgttaattt acgccaggat     900
gtaccgcctt tagatatctt aaatgttgta gactatgttc ctacgaatga agaaatttcg     960
cagcagaaaa ctcaaccaac agaccatggg gccgttggtg ttttcatct agacgatcat    1020 atttctccgg gcgaacaaag tcttaagcaa acaattggtg ataaagcaga tcttaaggt     1080 aaagatggca atagcagccc tcaggaattt aaattaataa ctgatgaaga gcaattgaga    1140
agagcgtcac aagaactgaa ggatgaggaa aaggatgccg agtctccttg gcaagcaatc    1200
ttgctgttac caaaaggtta taaggagggg gtagattttc gaaataaacc agtggcccac    1260
acggattcat ctttcaataa tgaagacaca attactcatt cagagttaga agtgaacacc    1320 ggatccccctt cgcaagaaag cggatcactt aatgaagctg gcataggcat aatgcaaccc    1380
atgtcggaag tacaaagaag aaaagaagac gttacgcccg catcaccaat attaacaagt    1440
agtcaaacgc cgcattactc aaactcgctt tataacgcac cttttgctgt ttcctctcca    1500
ccagatcctt taccaaacct ttttaccacc acaagtgaaa aagttttccc caaaattaat    1560
```

| | |
|---|---|
| gttttaatag ttgaagacaa cgtcatcaac caagctatct taggttcctt tctgaggaaa | 1620 |
| cacaaaatct catataaact ggctaaaaat ggtcaagaag ctgttaatat ttggaaggaa | 1680 |
| ggcggtcttc atttaatatt tatggattta cagctgcctg tcttgtctgg tatagaagct | 1740 |
| gccaagcaga ttagggactt cgaaaaacaa aatggcattg gcattcaaaa aagtctcaat | 1800 |
| aactcacact ccaatcttga aaaaggtact tcaaagagat tctctcaggc gcccgtgatt | 1860 |
| attgtagcat tgaccgcatc taactctcag atggataaaa gaaaagcact tctttctggt | 1920 |
| tgtaacgact acctgactaa accagtgaat ttacactggc ttagtaagaa aattacagag | 1980 |
| tggggatgta tgcaagcctt gattgatttt gacagctgga agcagggaga aagccggatg | 2040 |
| accgacagtg ttttggttaa atctccacag aaacctattg caccttccaa ccctcactca | 2100 |
| ttcaaacaag cgacatctat gaccccctaca cacagcccag taagaaaaaa ttcaaacctc | 2160 |
| tcgcccactc aaatagaatt gtgagtttgg ttgtaccgtg tagaggacat tatgatagaa | 2220 |
| tgtaacgat | 2229 |

<210> SEQ ID NO 2
<211> LENGTH: 1449
<212> TYPE: DNA
<213> ORGANISM: Saccharomyces cerevisiae

<400> SEQUENCE: 2

| | |
|---|---|
| ctctagataa gcaaacacaa ttatttcaa aaaaatttct gctaaatggg tagaagaaaa | 60 |
| attgaaattg aacctatcaa agatgataga atcgtacag ttactttcat aaagcgaaaa | 120 |
| gcaggactgt ttaaaaaggc tcatgaattg tcagtacttt gccaagtaga cattgctgtc | 180 |
| attattttag gatccaataa tacattctac gaatactctt ctgttgatat gagtaacctg | 240 |
| cttaatgttc atcaaaacaa cactgatctt cctcataata tcatagaacc atctgattat | 300 |
| ggtgactatg tgaaaaaacc acgtgttgtt ctgaatgaaa ggaagcgcag gcgaagaaga | 360 |
| gcaaccgtgt tgcgaccagc ttctcattct gggagttgta cagtttcgag tcaagatccc | 420 |
| tccagtgtac aaaacaatgg gaatttaagc gctccgttgg cgtcaaatga cgccgggaac | 480 |
| gctggtgtaa gtacaccatt ggtgcattgc cacggagcaa tatcacgtag cggatccaat | 540 |
| cattctgact gtgcaagaaa tagtgcagat tatcaaatgt tgcaaggcgg tttaaattct | 600 |
| ggtgggagtt tcatgctaa tgattataaa gaaagcgtag accaacagca tgttgcaaac | 660 |
| gaggctattc ataggaattt tatgaacaag aggattaggc cggatactca tttactactt | 720 |
| tctgaatcta accactctaa ttatcataat ttttacccgt cgccttacga gaatttgcca | 780 |
| aagccttcat tgcctgcaag tttagtgggc aatattccat cctttcaatc gcaatttgta | 840 |
| caggttattc cggcaaatag taacccaatg ggaaaaggat ttaatgggac gggtgacagc | 900 |
| gagagctttg aagcaaagca aagatacac ccgacagttg ctatatcaaa acttttggaa | 960 |
| ggtccagctc cagtgcaggc gatggtccat cacctgcacc aactgaacag caatagagga | 1020 |
| aagctctcag ggaagccata tttaaagcta aatattccga aggccacaaa tgacgcttgc | 1080 |
| cagaggtcgc cagcaatgta ttcaggaacc gcatcaccga aaacggatgt acaagccact | 1140 |
| cccaatcaaa tgctcgccag caacatgtcc tccctctttt ctcgttcaaa gttttgggga | 1200 |
| ttcaagaaca atgatatgga cgacttatat cataatggcc gatgtggcag cacttatgta | 1260 |
| aataacaaaa cattctttct gaaaccgcca attggaagac cgcctaaatt tccgaaaagc | 1320 |

```
ccgtcttcat ctattgtggt ttttccttcc tcggtagcta gttcaacttt gaaatccacg    1380
agttcgacaa actctccaga ttaatgaatc gctttctagc tactttttac tacaagaaag    1440
cattcgctt                                                            1449
```

INDUSTRIALLY USEFUL STRAINS OF YEAST

CROSS-REFERENCE TO RELATED APPLICATIONS

This application is a National Stage Application of PCT/IN2018/050792, filed on Nov. 28, 2018, which claims benefit of Application No. 201721044702, filed in India on Dec. 12, 2017, which Applications are incorporated herein by reference. A claim of priority to all, to the extent appropriate, is made.

SEQUENCE LISTING

The instant application contains a Sequence Listing which has been submitted electronically in ASCII format and is hereby incorporated by reference in its entirety. Said ASCII copy, created on Jun. 11, 2020, is named 4066_014USWO_SL.txt and is 5,371 bytes in size.

THE FIELD OF INVENTION

The invention relates to a method for the preparation of industrially useful strains of yeast *Saccharomyces cerevisiae* and the strain prepared by said method. In particular the invention relates to the creation of double mutant strains of said yeast that shows high ethanol conversion efficiency and substantially reduced acetic acid and glycerol production during fermentative production of ethanol from a sugar-based feedstock.

INTRODUCTION

The energy demand has been increasing continuously and one of the ways to address it is by increasing the production of renewable liquid fuels like ethanol. Ethanol can serve as a supplement to fuel supply as it is a good substitute for gasoline or can be blended with it. This percentage of blending ranges from about 5% to 95% of gasoline.

Mostly ethanol is produced by fermentation of sugars [largely sucrose or glucose] using the yeast *S. cerevisiae*. The major raw material required for ethanol production is hexose sugars. Sugarcane molasses is a widely used sucrose based feedstock for ethanol production in countries like India which is the second largest sugarcane producing country in the world. The molasses is a by-product of sugar processing unit and it contains about 45 to 50% of fermentable sugars. But the cost of this feedstock is a major challenge in ethanol production as it accounts up to 70% of the total production costs. It is therefore necessary to utilize the available carbon source to its maximum by increasing the ethanol yield from available sugars. Glycerol, acetic acid, and acetaldehyde are the by-products which are formed during ethanol production by fermentation. Here about 4 to 6% carbon flux can go towards glycerol and acetic acid production.

To solve the problem of conversion of maximum sugar to ethanol, a reduction in glycerol or acetic acid production is one of the ways to achieve higher ethanol yields. Even a slight diversion of carbon flux from glycerol or acetic acid to ethanol may have huge impact at the industrial scale where ethanol is produced in terms of millions of liters.

Glycerol is an intermediate metabolite in glycolysis pathway. *S. cerevisiae* produces this glycerol for two purposes. First purpose is to balance the high osmotic stress. Here glycerol production and accumulation in cells exposed to the high osmotic conditions helps to restore the turgor pressure and thus maintain the cellular integrity. Second purpose is to maintain the redox balance in the anaerobic growth conditions. These important roles of glycerol in yeast impose a challenge in reducing glycerol production by flux management as it directly hampers the growth of the organism. The glycerol synthesis thus cannot be completely eliminated but it can be reduced significantly and one of the approaches reported to reduce glycerol yield during ethanol production is genetic modification of the yeast strains. A major rate limiting step in glycerol synthesis is conversion of dihydroxyacetone phosphate to glycerol-3-phosphate by the enzyme glycerol-3-phosphate dehydrogenase, which is encoded by two isogenes GPD1 and GPD2. The deletion of GPD1 reduces the glycerol production; however, it causes an osmosentitive phenotype therefore causes negative effects on the growth and other fermentation properties like sugar consumption and product formation rate.

Acetic acid is produced by *S. cerevisiae* by oxidation of acetaldehyde to acetate using aldehyde dehydrogenases. *S. cerevisiae* has five acetaldehyde dehydrogenase isogenes—ald2, ald3, ald4, ald5 and ald6. They are all cofactor dependent, either $NAD^+$ or $NADP^+$. All of the genes are also regulated differently and may function under different conditions.

DETAILED DESCRIPTION

Figure 1:
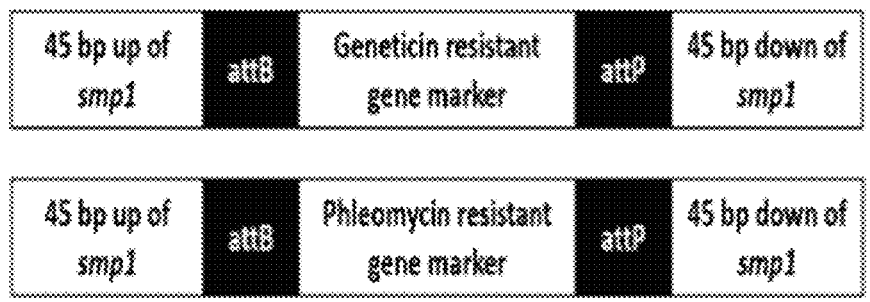
FIG. 1 is a schematic of the deletion cassettes for SMP1 gene.

The yeast *S. cerevisiae* possesses several pathways for the cell to adapt to different environmental stresses. Most of these pathways belong to class of mitogen activated protein kinase (MAPK) cascades. The high osmolarity glycerol (HOG) pathway is a MAPK pathway, which has a role in adaptation to hyperosmotic stress. Upstream of the HOG pathway are two branches, sln1 and sho1, both senses the osmolarity, but the sln1 branch is reported to be more sensitive.

The present invention related to the deletion of ssk1 gene which blocks the sln1 signaling branch which lead to delayed nuclear localization response of activated hog1. Present invention also relates to the deletion of transcription factor SMP1. SMP1 is a hog1 dependent gene strongly induced upon osmotic stress. SMP1 encodes for a transcription factor belonging to the MEF2c family and strongly dependent on hog1.

Yeast Strains and Growth Conditions

In one of the embodiment of present invention, *Escherichia coli* (*E. coli*) DH5α is used to multiply and carry plasmids. The *S. cerevisiae* strain (PRY201W) is used as wild type base strain. It is a diploid strain and widely used for the ethanol production at large industrial scales. The yeast peptone dextrose (YPD) medium is used for pre-culturing and maintaining the yeast strains. It is consisted of about 1% w/v of yeast extract, about 2% w/v of peptone and about 2% w/v of dextrose with initial pH 5 to 5.5. YPD agar contains about 2% agar in addition to other components. The sugarcane molasses medium consisted of sugarcane molasses as required and urea at about 0.05% w/v. All other methods used are standard methods used in the art.

Construction of Yeast Mutants:

Deletion [or inactivation] of genes from parent wild type strain is carried out by replacing the desired locus with deletion cassette by homologous recombination of about 40-45 bp in both upstream and downstream regions of desired locus that is to be deleted. The deletion cassette consisted of a marker gene flanked by attB and attP sites recognized by phiC31 integrase enzyme of the bacteriophage phiC31. The cassette has a 45-bp homologous element to upstream region of the gene to be deleted at its 5' end and a 45-bp homologous element to downstream region at its 3' end. The marker genes were simply an antibiotic resistant gene for the yeast. Parent yeast is a diploid yeast strain. The selected colonies on the antibiotic plate are screened with PCR, and clones where both alleles of the desired gene are deleted were selected. The selected stable engineered yeast mutants are allowed to recover further on YPD at about 30° C., at about 150 rpm overnight and plated on YPD agar with respective antibiotic for selection. Said mutant cultures are used further for fermentation of molasses to produce ethanol. The genotypes of the engineered yeast strains are given in Table A. The detailed procedures for creation of mutants are listed in Example 4 to 6.

TABLE A

LIST OF YEAST STRAINS.

| Name | Description/genotype | Source |
| --- | --- | --- |
| PRY201W | S. cerevisiae strain | PRAJ internal collection |
| PRY201A | PRY201WΔsmp1 | Disclosed in Example 4 |
| PRY201B | PRY201WΔssk1 | Disclosed in Example 5 |
| PRY201AB | PRY201WΔsmp1, Δssk1 | Disclosed in Example 6 |

The strain PRY201A is constructed by deleting both the alleles of smp1 gene from parent yeast strain, PRY201W. The deletion was made by replacing both alleles of smp1 gene by deletion cassettes containing antibiotic selection marker genes in two steps and then excising out the marker genes in the third step. The colonies are selected on YPD agar plates with 200 µg/ml of geneticin and 25 µg/ml of phleomycin. The growing colonies are again screened by PCR to verify replacement of alleles by the deletion cassette. The antibiotic resistance genes were then looped out by transient expression of the PhiC 31 integrase enzyme from the selected colonies. The gene deletion and marker excision was further verified and confirmed by the DNA sequencing. Above procedure is then repeated for the construction of PRY201B. The strain PRY201B is constructed by deleting both the alleles of ssk1 gene from PRY201W. The strain PRY201AB was constructed by deleting both the alleles of ssk1 gene from PRY201A. The ssk1 gene has DNA sequence of SEQ ID NO: 1 of S. cerevisiae. The smp1 gene has DNA sequence of SEQ ID NO: 2 of S. cerevisiae.

Fermentation Studies

The above mutant yeast strains are pre-cultured twice before fermentation. First pre-culture is made by culturing yeast in YPD medium at about 30° C. for about 18 hours under shaking conditions at about 150 rpm. Second pre-culture is prepared with same growth parameters in sterile sugarcane molasses medium having about 5% w/w of fermentable sugar and about 10% v/v of first pre-culture broth as inoculum. Said second pre-culture having about $10^8$ cells/ml is used as the inoculum for the large-scale fermentations. The fermentation is carried out using unsterilized sugarcane molasses consisting of about 16% w/w fermentable sugar and about 10% v/v second pre-culture broth as inoculum at about 30° C. and 150 rpm. Samples of fermentation broth at different time points were analyzed for residual sugar, acetic acid, ethanol and glycerol using standard high performance liquid chromatography methods.

Said PRY201A produces about 3% to 5% more ethanol than parent strain, PRY201W. Said PRY201B also produces about 4% to 6% more ethanol than parent strain, PRY201W. While said double mutant PRY201AB produces about 6% to 9% more ethanol than the parent, PRY201W in identical fermentation conditions.

In another embodiment of the invention, PRY201A shows up to 3% increase in glycerol production than the parent strain PRY201W. But PRY201B and PRY201AB produces less glycerol than the parent strain. Glycerol is reduced up to 21% in PRY201B and up to 31% in PRY201AB than the parent strain PRY201W.

In another embodiment of the invention, acetic acid also reduced in modified strain than the parent, PRY201W. Said mutant strains produced between about 40% to about 70% less acetic acid compares with the parent strain PRY201W.

Spent Wash Recycle During Fermentation

After completion of the fermentation, the fermented broth is distilled and the bottom stream from the distillation unit, known as spent wash, is recycled back into the fermentor to save on fresh water requirement of the process. As modified strain produces lesser acetic acid, the amount of spent wash recycled increased to about 30% of the fresh water requirement. For parent strain, due to the high concentration of acetic acid, only about 18% of the fresh water requirement could be substituted and if about 30% of spent wash is recycled then a significant drop in ethanol yield with increase in glycerol and acetic acid yields is observed.

EXAMPLES

Examples provided below give a wider utility of the invention without any limitations as to the variations that may be appreciated by the person skilled in the art. A non-limiting summary of various experimental results is given in the examples, which demonstrate the advantageous and novel aspects of the modified strains over the parent strain based on the comparative data from experimentation in shake flask fermentation, fermentation in bio reactor and commercial level fermentation with spent wash recycled during the fermentation.

Example 1: Yeast Strains and Culturing Media

The YPD medium used for pre-culturing consisted of yeast extract 1% w/v, peptone 2% w/v, dextrose 2% w/v with initial pH 5 to 5.5. YPD agar had 2% agar in addition to yeast extract 1% w/v, peptone 2% w/v and dextrose 2% w/v. The sugarcane molasses medium consisted of sugarcane molasses as required and urea at about 0.05% w/v. All other methods used are standard methods used in the art. The basic or wild type yeast used is named PRY201W. The double mutant strain is named PRY201AB and is also known as X2P3 in the internal records.

Example 2: Identity of Genes

The genes referred as ssk1 and smp1 are described herein below. The ssk1 gene from *S. cerevisiae* has an SGD ID of S000003996 and a systematic name of YLR006C. The gene has about 2139 base pairs of nucleotides and the transcribed protein has 712 amino acids in the polypeptide. According to the yeast genome database, SSK1p is a cytoplasmic phosphorelase intermediate osmosensor and regulator.

The smp1 gene in *S. cerevisiae* has an SGD ID of S000000386 and a systematic name of YBR182C. The gene has about 1359 base pairs of nucleotides and the transcribed protein has 452 amino acids in the polypeptide. According to the yeast genome database, SMP1p is a MADS-box transcription factor involved in osmotic stress response.

Example 3: Analytical Methods

Sugars were analyzed by using standard high performance liquid chromatography methods. The fermentation samples were loaded on Biorad Aminex HPX-87N columns. The column temperature was maintained at about 85° C. About 0.01 M disodium hydrogen phosphate was used as the mobile phase at a flow rate of about 0.6 ml/min. The RI detector maintained at about 40° C. was used for sugar detection. The metabolites like ethanol, acetic acid and glycerol were also analyzed by using standard high performance liquid chromatography methods. The fermentation samples were loaded on Biorad Aminex HPX-87H columns. The column temperature was maintained at 55° C. About 0.005 M sulphuric acid was used as the mobile phase at a flow rate of about 0.6 ml/min. The RI detector maintained at 40° C. was used for detection of ethanol, acetic acid and glycerol.

Example 4: Construction of PRY201A

The strain PRY201A was constructed by deleting both the alleles of smp1 gene from parent yeast strain, PRY201W. The smp1 gene sequence is as per SEQ. ID No. 2 or any gene with sequence homology about 50% to SEQ. ID No. 2 as listed in Example 14. The deletion was made by replacing both alleles of smp1 gene by deletion cassettes containing antibiotic selection marker genes in two steps and then excising out the marker genes in the third step. In the first step, PRY201W was transformed with a deletion cassette having geneticin resistance gene marker as shown in FIG. 1. The transformants were plated on YPD agar plates with 200 µg/ml of geneticin and incubated at 30° C. to allow growth. The growing colonies were screened by PCR to verify deletion. Selected colony had one of the alleles of smp1 replaced with the deletion cassette. In the second step, the selected colony was again transformed with another deletion cassette which had phleomycin resistance gene marker as shown in FIG. 1. The colonies were selected on YPD agar plates with 200 µg/ml of geneticin and 25 µg/ml of phleomycin. The growing colonies were again screened by PCR to verify replacement of the second allele by the deletion cassette. The antibiotic resistance genes were then looped out by transient expression of the PhiC 31 integrase enzyme from the selected colonies. The gene deletion and marker excision was further verified and confirmed by the DNA sequencing. The inactivation of smp1 did not causing no adverse effect on physiology of said mutant strain.

Example 5: Construction of PRY201B

Figure 2:
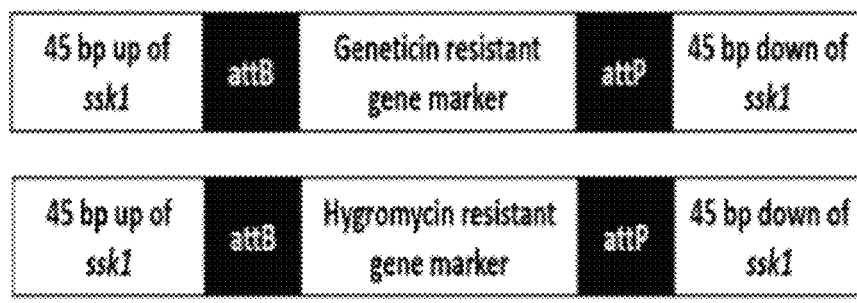
FIG. 2 is a schematic of the deletion cassettes for SSK1 gene.
Figure 3:
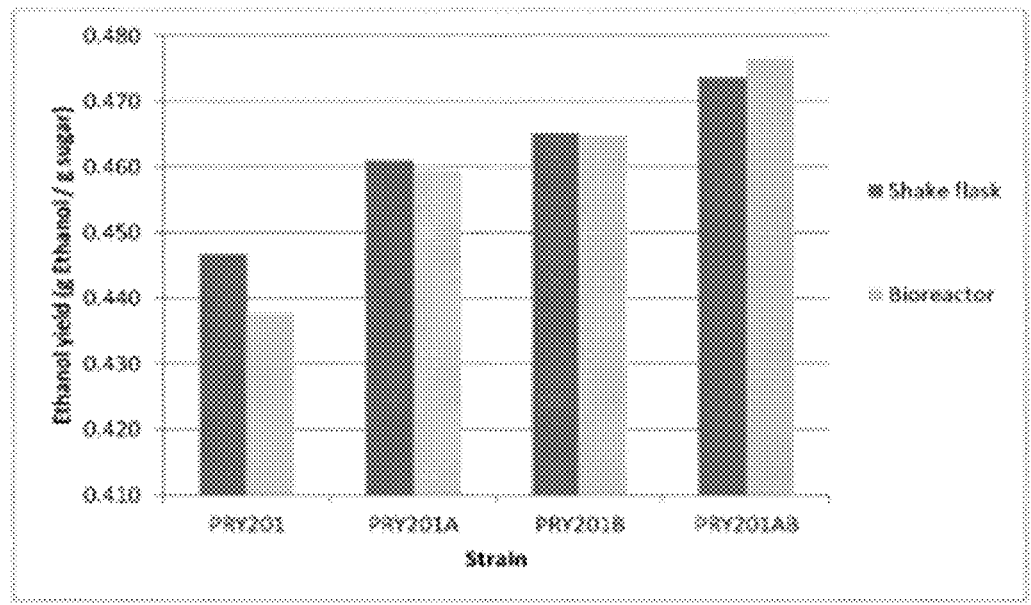
FIG. 3 is a histogram showing the increase in ethanol yields in the mutant yeast strains relative to the unmodified strain.
Figure 4:
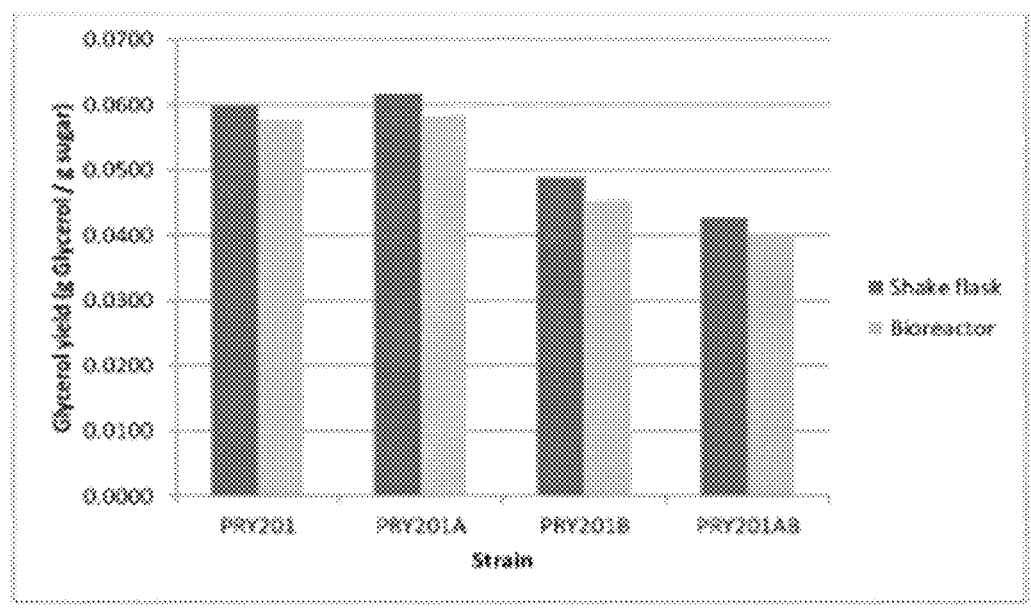
FIG. 4 is a histogram showing the decrease in glycerol yields in the in the mutant yeast strains relative to the unmodified strain.
Figure 5:
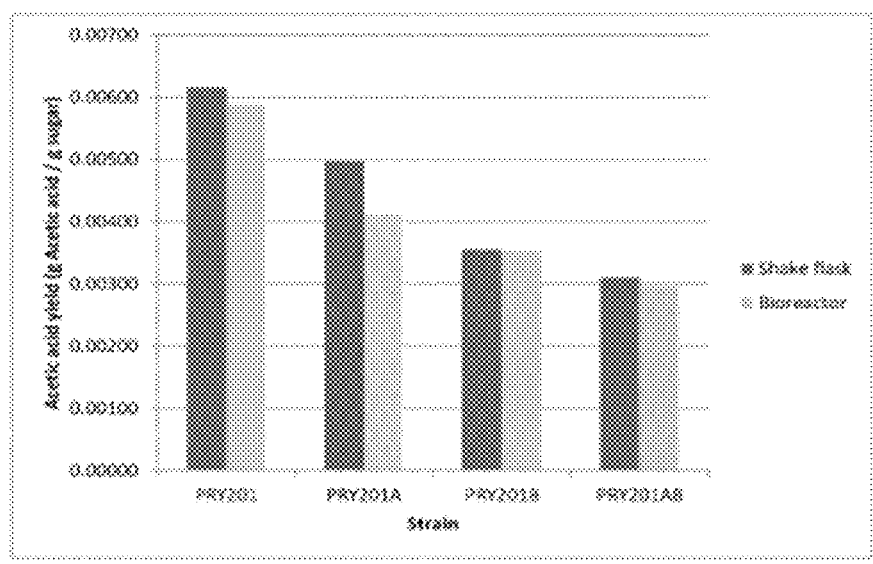
FIG. 5 is a histogram showing the decrease in acetic acid yields in the in the mutant yeast strains relative to the unmodified strain.

The strain PRY201B was constructed by deleting both the alleles of ssk1 gene from parent yeast strain, PRY201W. The ssk1 gene sequence is as per SEQ. ID No. 1 or any gene with sequence homology about 50% to SEQ. ID No. 1 as listed in Example 14. The deletion was made by replacing both alleles of ssk1 gene by deletion cassettes containing antibiotic selection marker genes in two steps and then excising out the marker genes in the third step. In the first step, PRY201W was transformed with a deletion cassette having geneticin resistance gene marker as shown in FIG. 2. The transformants were plated on YPD agar plates with about 200 µg/ml of geneticin and incubated at about 30° C. to allow growth. The growing colonies were screened by PCR to verify deletion. Selected colony had one of the alleles of ssk1 replaced with the deletion cassette. In the second step, the selected colony was again transformed with another deletion cassette which had hygromycin resistance gene marker. The colonies were selected on YPD agar plates with about 200 µg/ml of geneticin and about 300 µg/ml of hygromycin. The growing colonies were again screened by PCR to verify replacement of the second allele by the deletion cassette. The antibiotic resistance genes were then looped out by transient expression of the PhiC 31 integrase enzyme from the selected colonies. The gene deletion and marker excision was further verified and confirmed by the DNA sequencing. The inactivation of ssk1 did not causing no adverse effect on physiology of said mutant strain.

Example 6: Construction of PRY201AB

The strain PRY201AB was constructed by deleting both the alleles of ssk1 gene from PRY201A. The deletion was made by replacing both alleles of ssk1 gene by deletion cassettes containing antibiotic selection marker genes in two steps and then excising out the marker genes in the third step as described in Example 4. Table 1 illustrates the list of yeast strains disclosed herein. The double inactivation of smp1 and ssk1 did not causing no adverse effect on physiology of said mutant strain.

TABLE 1

LIST OF YEAST STRAINS.

| Name | *S. cerevisiae* Genotype | Source |
| --- | --- | --- |
| PRY201W | Wild Type | PRAJ internal collection |
| PRY201A | PRY201WΔsmp1 | Disclosed herein |
| PRY201B | PRY201WΔssk1 | Disclosed herein |
| PRY201AB | PRY201WΔsmp1, Δssk1 | Disclosed herein |

Example 7: Shake Flask Fermentation Studies

The yeast strains were pre-cultured twice before fermentation. First pre-culture was made by culturing yeast in 100 ml Erlenmeyer flask with about 40 ml sterile YPD medium at about 30° C. for 18-20 hours (approximate $OD_{600}$ of 20) under shaking conditions of about 150 rpm. Second pre-culture was prepared in sterile sugarcane molasses medium with about 5% w/w of fermentable sugar and about 10% v/v of first pre-culture broth as inoculum. Second pre-culture had working volume of about 100 ml in 250-ml Erlenmeyer flask and cultured for 18-20 hours (to approximate cell density $\geq 2.5 \times 10^8$ cells/ml) with shaking at about 150 rpm. The main fermentation in shake flask was done with working volume of about 500 ml in a 1-liter Erlenmeyer flask. Here unsterilized sugarcane molasses medium was utilized consisting of about 16% w/w fermentable sugar and about 10% v/v second pre-culture broth as inoculum. Fermentation was done at about 30° C. under shaking conditions of about 150 rpm. Samples of fermentation broth at different time points were analyzed for residual sugar, acetic acid, ethanol and glycerol.

Example 8: 1-L Bioreactor Fermentation Studies

The fermentation in 1-L bioreactors was performed in fed-batch mode. Bench top fermentor with vessel capacity of 1.3-L was used in these experiments. The inoculum was prepared by pre-culturing yeast strains twice as disclosed in Example 6. The bioreactor was initially loaded with about 100 ml second pre-cultured broth as inoculum in about 400 ml water and about 0.5 g of urea. After this, about 500 ml of diluted sugarcane molasses consisting of about 32% w/w fermentable sugars was continuously dispensed in the bioreactor at a flow rate of about 0.55 ml/min to complete the feeding in about 16 h. The temperature in the bioreactor was maintained at about 30° C. with help of the water jacket and mixing was achieved throughout the fermentation process by continuous agitation at about 250 rpm. Samples were taken at regular intervals and analyzed for residual sugars, acetic acid, ethanol and glycerol.

Example 9: Ethanol Production

The results comparing the ethanol yields produced by all the strains are given in Table 2. PRY201A shows about 3% increase in shake flask and about 5% increase in bioreactor over the parent, PRY201. PRY201B shows about 4% increase in shake flask and about 6% increase in bioreactor over the parent, PRY201W. PRY201AB shows about 6% increase in shake flask and about 9% increase in bioreactor over the parent, PRY201W.

TABLE 2

ETHANOL YIELDS (G OF ETHANOL/G OF SUGAR [% DIFFERENCES ARE GIVEN IN BRACKETS]).

| SIZE | PRY201W | PRY201A | PRY201B | PRY201AB |
|---|---|---|---|---|
| Shake flask | 0.447 [0] | 0.461 [3.1] | 0.465 [4.0] | 0.474 [6.0] |
| Bioreactor | 0.438 [0] | 0.459 [4.8] | 0.465 [6.2] | 0.476 [8.7] |

Example 10: Glycerol Production

The results comparing the glycerol yields produced by all the strains are given in Table 3. PRY201A shows a 3% increase in shake flask and 1% increase in bioreactor over the parent, PRY201W. PRY201B shows an 18% decrease in shake flask and 21% decrease in bioreactor over the parent, PRY201W. PRY201AB shows about 12% decrease in shake flask and 31% decrease in bioreactor over the parent, PRY201W.

TABLE 3

GLYCEROL YIELDS (G OF GLYCEROL/G OF SUGAR [% DIFFERENCES ARE GIVEN IN BRACKETS]).

| SIZE | PRY201W | PRY201A | PRY201B | PRY201AB |
|---|---|---|---|---|
| Shake flask | 0.0598 [Control] | 0.0616 [3.0] | 0.0488 [−19.4] | 0.0527 [−12.0] |
| Bio-reactor | 0.0576 [Control] | 0.0582 [1.1] | 0.0453 [−22.4] | 0.0400 [−31.6] |

Example 11: Acetic Acid Production

The results comparing the acetic acid yields produced by all the strains are given in Table 4. PRY201A shows a 19% decrease in shake flask and 30% decrease in bioreactor over the parent, PRY201W. PRY201B shows a 42% decrease in shake flask and 40% decrease in bioreactor over the parent, PRY201W. PRY201AB shows a 50% decrease in shake flask and 50% decrease in bioreactor over the parent, PRY201W.

TABLE 4

ACETIC ACID YIELDS (G OF ACETIC ACID/G OF SUGAR [% DIFFERENCES ARE GIVEN IN BRACKETS]).

| SIZE | PRY201W | PRY201A | PRY201B | PRY201AB |
|---|---|---|---|---|
| Shake flask | 0.00616 [Control] | 0.00496 [−19.5] | 0.00355 [−42.4] | 0.00310 [−50.0] |
| Bio-reactor | 0.00588 [Control] | 0.00412 [−30.0] | 0.00353 [−40.0] | 0.00294 [−50.0] |

Example 12: Fermentation at Commercial Scale

Fermentation using cane molasses medium was carried out at commercial scale in a fermentor of about 1-KL working volume. The comparative data were collected for an existing commercial strain X and PRY201AB on the ethanol, glycerol and acetic acid production yields. The results are shown in Table 5. The fermentation with the strain PRY201AB showed about 4% increase in ethanol yield over the commercial strain X. It further showed about 73% reduction in acetic acid compared to strain X. However, an increase of about 14% in glycerol was seen when using PRY201AB as compared to strain X.

TABLE 5

COMPARISON OF YEAST STRAINS AT A COMMERCIAL SCALE [% DIFFERENCES ARE GIVEN IN BRACKETS].

| Strain | Ethanol yield (g/g of sugar) | Glycerol yield (g/g of sugar) | Acetic acid yield (g/g of sugar) |
|---|---|---|---|
| Strain X | 0.449 [Control] | 0.0383 [Control] | 0.0163 [Control] |
| PRY201AB | 0.469 [4.3] | 0.0437 [12.4] | 0.0044 [−73.0] |

Example 13: Spent Wash Recycle

On the completion of fermentation in a 1-KL fermentor at the commercial scale, the fermented broth is distilled and the bottom stream from the distillation unit, known as spent wash, is recycled back to the fermentor to save on fresh water requirement of the process. As shown in Table 6, due to the high concentration of acetic acid, only about 18% of the fresh water requirement is substituted with spent wash when commercial strain X was used. However, with strain PRY201AB producing lesser acetic acid, the amount of spent wash recycled increased to about 30% of the fresh water requirement. However at about 30% of spent wash recycled, strain X shows a drop in ethanol yield with increase in glycerol and acetic acid yields.

TABLE 6

COMPARISON OF YEAST STRAINS FOR SPENT WASH RECYCLED AT COMMERCIAL SCALE.

| Strain | Spent wash recycle as percentage of water requirement [%] | Ethanol yield (g/g of sugar) | Glycerol yield (g/g of sugar) | Acetic acid yield (g/g of sugar) |
|---|---|---|---|---|
| PY201AB | 29 | 0.469 | 0.0597 | 0.0089 |
| Strain X | 28 | 0.429 | 0.0659 | 0.0155 |
| Strain X | 18 | 0.464 | 0.0627 | 0.0136 |

Example 14: Sequences of Genes

The ssk1 DNA sequence is SEQ ID NO. 1 [total 2229 nucleotides listed]:

CTGCTGTAAATCAAAAACGAATCGATTTTGGGGAGACAAGTAAAAATGCT
CAATTCTGCGTTACTGTGGAAGGTTTGGCTACGAATAGACAACTCCACTG
ATGAAGTAAACCAACCAATTGCTGTACAGTTCGATGAAATAGATACTGTT
GATGATTTGAAGAGCAGGTTTTTTCAGAAACTGAGTTCGACTCGATGGCG
AGAAATTAACGATAATGCTTCCATTGCAATAGGCCTCTACGCACCTAAAT
TTGACAATCAAGCCGACAATACCAGTAGTAACAACACTAACGATAATAGT
TGTCGAAGTAAGAGTAACGGTGCTGGAAGTGGCGCCAACCTTTCCGTTAA
TAGCAATACCAAGAGTTCAGTGAGCCCCACAGCAGGATCATTTGGTCTTT
CAAAAGACCTTGCAAAGGACAGGAATGTTCTCCAGCATCCTAAACCTACG
CAGAAAAGAGGAGCATTATACGACGCCTTTGCCGCCGCGCCGACAGTGGC
CGCGACTACCAATGTGGATTTTCCTCCCAACGAGGCGCCAATGCTAAGCC
CGCAAAGACCATACTCTACTAGTCCTAAACAGTTTCCAGCAACAACTAAA
AGTCCGTTACTGCGATTTGCCTCAGTCTCACCCTACCCTAAATTTCATCC
TGATAATCAAATTATGGCATCAGCTGGTCTTACATACGTCTCACCGCATA
ATAAAAATAAATACACAAGGCCGTTGATTAGAAAAGGTTTAAATTTCACC
ACAGAATCAGTTAATGATTGCACTTATAAAATCATCTTTGAACCGGATGA
ATTGGCTATTAACATATATAAGGAACTGTTCGGAACCATGGGTTCCCAAC
CTGCATCGCAGCCTTTGCTGATATTTTCGAATGTTAATTTACGCCAGGAT
GTACCGCCTTTAGATATCTTAAATGTTGTAGACTATGTTCCTACGAATGA
AGAAATTTCGCAGCAGAAAACTCAACCAACAGACCATGGGGCCGTTGGTG
TTTTTCATCTAGACGATCATATTTCTCCGGGCGAACAAAGTCTTAAGCAA
ACAATTGGTGATAAAGCAGATCTTAAAGGTAAAGATGGCAATAGCAGCCC
TCAGGAATTTAAATTAATAACTGATGAAGAGCAATTGAGAAGAGCGTCAC
AAGAACTGAAGGATGAGGAAAAGGATGCCGAGTCTCCTTGGCAAGCAATC
TTGCTGTTACCAAAAGGTTATAAAGGAGGGTAGATTTTCGAAATAAACC
AGTGGCCCACACGGATTCATCTTTCAATAATGAAGACACAATTACTCATT
CAGAGTTAGAAGTGAACACCGGATCCCCTTCGCAAGAAAGCGGATCACTT
AATGAAGCTGGCATAGGCATAATGCAACCCATGTCGGAAGTACAAAGAAG
AAAAGAAGACGTTACGCCCGCATCACCAATATTAACAAGTAGTCAAACGC
CGCATTACTCAAACTCGCTTTATAACGCACCTTTTGCTGTTTCCTCTCCA
CCAGATCCTTTACCAAACCTTTTTACCACCACAAGTGAAAAAGTTTTCCC
CAAAATTAATGTTTTAATAGTTGAAGACAACGTCATCAACCAAGCTATCT
TAGGTTCCTTTCTGAGGAAACACAAAATCTCATATAAACTGGCTAAAAAT
GGTCAAGAAGCTGTTAATATTTGGAAGGAAGGCGGTCTTCATTTAATATT
TATGGATTTACAGCTGCCTGTCTTGTCTGGTATAGAAGCTGCCAAGCAGA
TTAGGGACTTCGAAAAACAAAATGGCATTGGCATTCAAAAAAGTCTCAAT
AACTCACACTCCAATCTTGAAAAAGGTACTTCAAAGAGATTCTCTCAGGC
GCCCGTGATTATTGTAGCATTGACCGCATCTAACTCTCAGATGGATAAAA
GAAAAGCACTTCTTTCTGGTTGTAACGACTACCTGACTAAACCAGTGAAT
TTACACTGGCTTAGTAAGAAAATTACAGAGTGGGGATGTATGCAAGCCTT
GATTGATTTTGACAGCTGGAAGCAGGGAGAAAGCCGGATGACCGACAGTG
TTTTGGTTAAATCTCCACAGAAACCTATTGCACCTTCCAACCCTCACTCA
TTCAAACAAGCGACATCTATGACCCCTACACACAGCCCAGTAAGAAAAAA
TTCAAACCTCTCGCCCACTCAAATAGAATTGTGAGTTTGGTTGTACCGTG
TAGAGGACATTATGATAGAATGTAACGAT

The smp1 DNA sequence is SEQ ID NO. 2 [total 1449 nucleotides are listed]:

CTCTAGATAAGCAAACACAATTATTTTCAAAAAAATTTCTGCTAAATGGG
TAGAAGAAAAATTGAAATTGAACCTATCAAAGATGATAGAAATCGTACAG
TTACTTTCATAAAGCGAAAAGCAGGACTGTTTAAAAAGGCTCATGAATTG
TCAGTACTTTGCCAAGTAGACATTGCTGTCATTATTTTAGGATCCAATAA
TACATTCTACGAATACTCTTCTGTTGATATGAGTAACCTGCTTAATGTTC
ATCAAAACAACACTGATCTTCCTCATAATATCATAGAACCATCTGATTAT
GGTGACTATGTGAAAAAACCACGTGTTGTTCTGAATGAAAGGAAGCGCAG
GCGAAGAAGAGCAACCGTGTTGCGACCAGCTTCTCATTCTGGGAGTTGTA
CAGTTTCGAGTCAAGATCCCTCCAGTGTACAAAACAATGGGAATTTAAGC
GCTCCGTTGGCGTCAAATGACGCCGGGAACGCTGGTGTAAGTACACCATT
GGTGCATTGCCACGGAGCAATATCACGTAGCGGATCCAATCATTCTGACT
GTGCAAGAAATAGTGCAGATTATCAAATGTTGCAAGGCGGTTTAAATTCT
GGTGGGAGTTTTCATGCTAATGATTATAAAGAAAGCGTAGACCAACAGCA
TGTTGCAAACGAGGCTATTCATAGGAATTTTATGAACAAGAGGATTAGGC
CGGATACTCATTTACTACTTTCTGAATCTAACCACTCTAATTATCATAAT
TTTTACCCGTCGCCTTACGAGAATTTGCCAAAGCCTTCATTGCCTGCAAG
TTTAGTGGGCAATATTCCATCCTTTCAATCGCAATTTGTACAGGTTATTC
CGGCAAATAGTAACCCAATGGGAAAAGGATTTAATGGGACGGGTGACAGC
GAGAGCTTTGAAGCAAAGCAAAAGATACACCCGACAGTTGCTATATCAAA
TACTTTGGAAGGTCCAGCTCCAGTGCAGGCGATGGTCCATCACCTGCACC

-continued

```
AACTGAACAGCAATAGAGGAAAGCTCTCAGGGAAGCCATATTTAAAGCTA

AATATTCCGAAGGCCACAAATGACGCTTGCCAGAGGTCGCCAGCAATGTA

TTCAGGAACCGCATCACCGAAAACGGATGTACAAGCCACTCCCAATCAAA

TGCTCGCCAGCAACATGTCCTCCCCTCTTTCTCGTTCAAAGTTTTTGGGA

TTCAAGAACAATGATATGGACGACTTATATCATAATGGCCGATGTGGCAG

CACTTATGTAAATAACAAAACATTCTTTCTGAAACCGCCAATTGGAAGAC

CGCCTAAATTTCCGAAAAGCCCGTCTTCATCTATTGTGGTTTTTCCTTCC
```

-continued

```
TCGGTAGCTAGTTCAACTTTGAAATCCACGAGTTCGACAAACTCTCCAGA

TTAATGAATCGCTTTCTAGCTACTTTTTACTACAAGAAAGCATTCGCTT
```

The flanking regions for homologous recombination events are underlined and shown bold for the ssk1 and smp1 genes.

The invention as disclosed in the specification uses the biological material from India and an application for the necessary permission has been made to the component authority. The strain disclosed herein is deposited with MTCC for safe deposit of proprietary biological resources.

We claim:

1. A modified yeast strain for reduced production of fermentation by-products in the production of ethanol, comprising a modified yeast strain of a *Saccharomyces cerevisiae* yeast strain including smp1 gene and ssk1 gene wherein:
   (a) the modified yeast strain has both ssk1 gene and smp1 gene deleted; and
   (b) said deletions cause no adverse effect to the physiology of said strain.

2. The yeast strain of claim 1, wherein ssk1 gene has DNA sequence of SEQ ID NO:1.

3. The yeast strain of claim 1, wherein smp1 gene has DNA sequence of SEQ ID NO: 2.

4. The yeast strain of claim 1, wherein when used in a fermentation process, fermentation by-product acetic acid is produced up to 50% less per gram of sugar compared to the wild type *Saccharomyces* sp. yeast strain.

5. The yeast strain of claim 1, wherein when used in a fermentation process, fermentation by-product glycerol is produced up to 30% less per gram of sugar compared to the wild type *Saccharomyces* sp. yeast strain.

6. The yeast strain of claim 1, wherein when used in a fermentation process, fermentation product ethanol is produced up to 9% more per gram of sugar compared to the wild type *Saccharomyces* sp. yeast strain.

7. The yeast strain of claim 1, when used in a fermentation process, a spent wash produced is recyclable up to 30% in a next round of said-fermentation process.

8. A modified yeast strain for reduced production of fermentation by products in the production of ethanol, comprising a modified yeast strain of a *Saccharomyces cerevisiae*, wherein both ssk1 gene and smp1 gene of the yeast strain are deleted.

9. A method of modifying a yeast strain for reduced production of fermentation by-products in the production of ethanol, the method comprising:
   deleting smp1 gene and ssk1 gene from a yeast strain of a *Saccharomyces cerevisiae*, wherein the yeast strain produces glycerol during fermentation of sugars and includes a high osmolarity glycerol (HOG) pathway, wherein deleting the smp1 gene and ssk1 gene decreases acetic acid yield and increases ethanol yield in the production of ethanol.

10. The method of claim 9, wherein deleting the smp1 gene and ssk1 gene includes replacing both alleles of smp1 gene and ssk1 gene with deletion cassettes including antibiotic selection marker genes and excising out the marker genes.

11. The method of claim 9, wherein the ssk1 gene has DNA sequence of SEQ ID NO: 1.

12. The method of claim 9, wherein the smp1 gene has DNA sequence of SEQ ID NO: 2.

* * * * *